(12) United States Patent
Haubeck

(10) Patent No.: US 8,003,339 B2
(45) Date of Patent: Aug. 23, 2011

(54) METHOD FOR DETERMINING ENDOGLYCOSIDASE (HEPARANASE) ENZYME ACTIVITY

(76) Inventor: Hans Dieter Haubeck, Gau-Algesheim (DE)

( * ) Notice: Subject to any disclaimer, the term of this patent is extended or adjusted under 35 U.S.C. 154(b) by 261 days.

(21) Appl. No.: 12/513,837

(22) PCT Filed: Oct. 13, 2007

(86) PCT No.: PCT/EP2007/008905
§ 371 (c)(1),
(2), (4) Date: Jun. 1, 2009

(87) PCT Pub. No.: WO2008/055575
PCT Pub. Date: May 15, 2008

(65) Prior Publication Data
US 2010/0120065 A1 May 13, 2010

(30) Foreign Application Priority Data
Nov. 7, 2006 (EP) .................................... 06023091

(51) Int. Cl.
*G01N 1/00* (2006.01)
*G01N 33/53* (2006.01)

(52) U.S. Cl. ............ 435/7.21; 435/2; 435/7.1; 436/501; 436/518; 436/522; 422/50

(58) Field of Classification Search .................. None
See application file for complete search history.

(56) References Cited

FOREIGN PATENT DOCUMENTS
WO    WO 98/03638 A1    1/1998

OTHER PUBLICATIONS

Behzad, F. and Brenchley, P.E.C. 2003 "A multiwell format assay for heparanase" *Analytical Biochemistry* 320:207-213.
Freeman, C. and Parish, C.R. 1997 "A rapid quantitative assay for the detection of mammalian heparanase activity" *Biochem J* 325:229-237.

*Primary Examiner* — Lisa Cook
(74) *Attorney, Agent, or Firm* — Knobbe Martens Olson & Bear LLP

(57) ABSTRACT

The present invention provides a method for determining endoglycosidase activity, and in particular of the heparanase type, in a sample, and also a method for detecting compounds that modulate the activity of endoglycosidases and in particular endoglycosidases of the heparanase type.

23 Claims, 3 Drawing Sheets

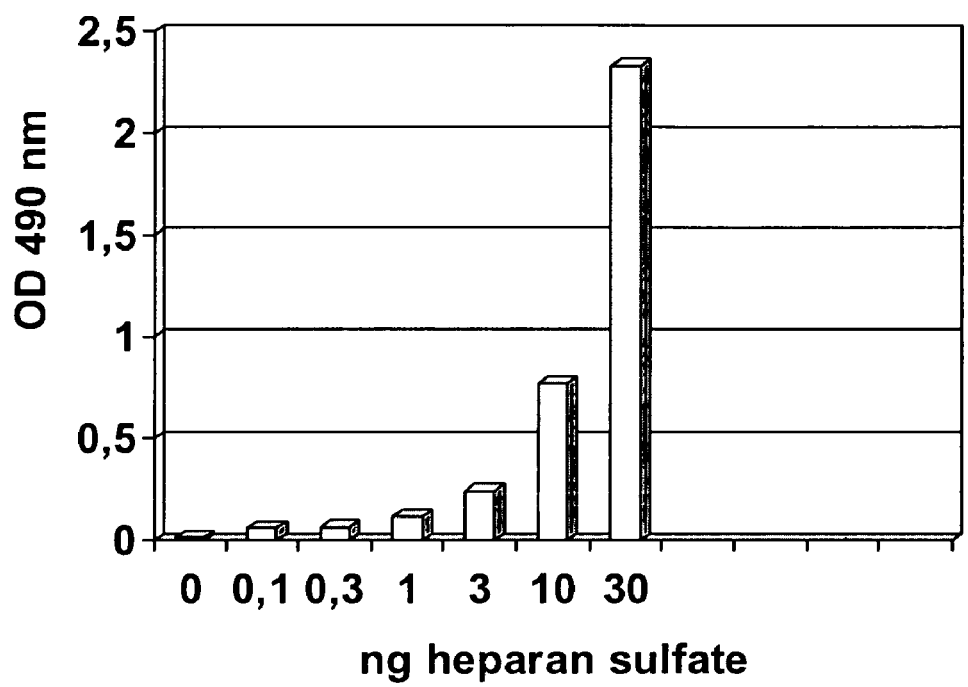
Fig. 1 Dose-dependent binding of biotin-labeled heparan sulfate to protamine

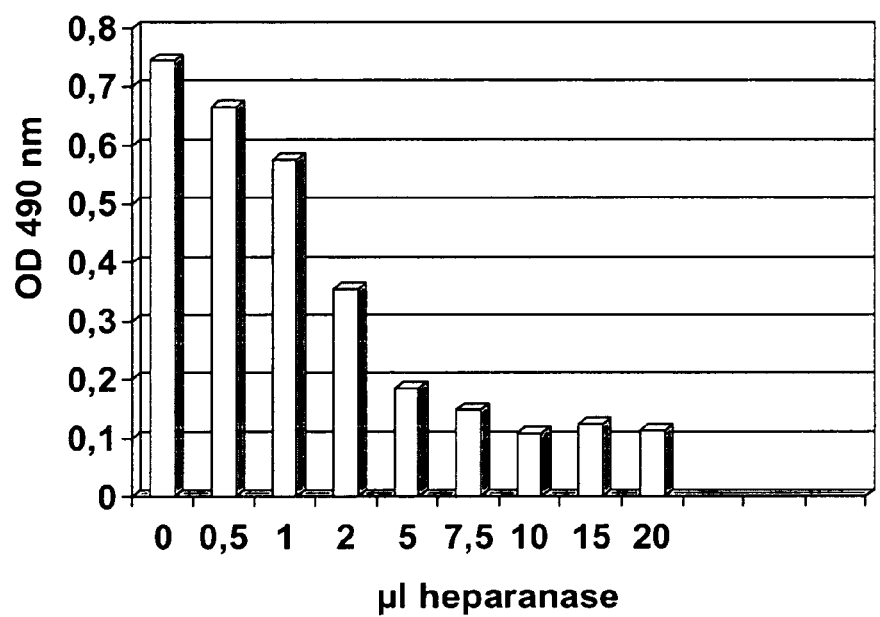
Fig. 2 Dose-dependent degradation of biotin-labeled heparan sulfate by human heparanase from PMN

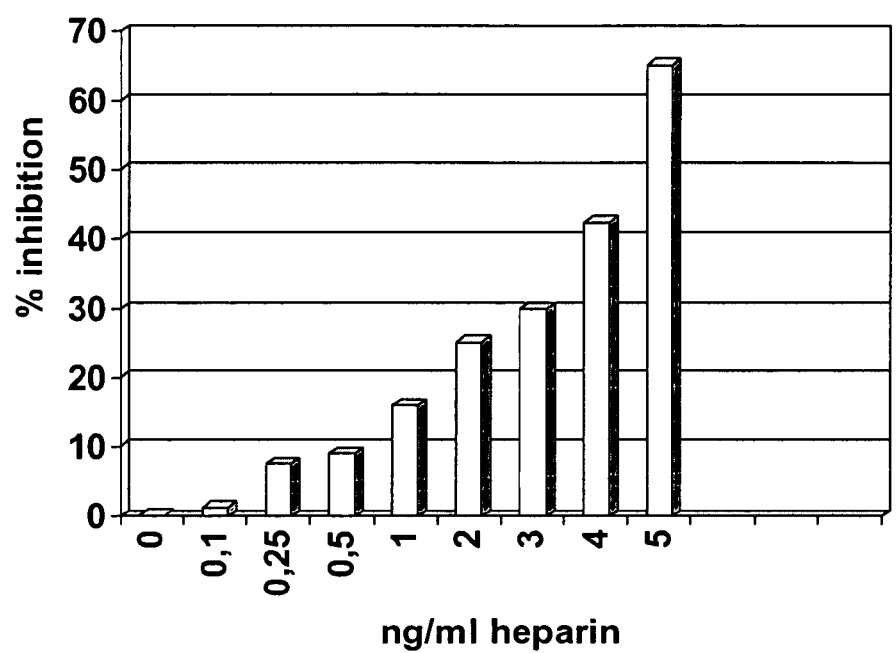
Fig. 3 Inhibition of heparanase activity by heparin

METHOD FOR DETERMINING ENDOGLYCOSIDASE (HEPARANASE) ENZYME ACTIVITY

RELATED APPLICATIONS

This application is a U.S. National Phase of International Application No.: PCT/EP2007/008905, filed Oct. 13, 2007, designating the U.S. and published in English on May 15, 2008 as WO 2008/055575 A1, which claims the benefit of European application No. 06023091.9, filed Nov. 7, 2006.

FIELD AND STATE OF THE ART

The present invention relates to a method for determining endoglycosidase enzyme activity, in particular of the heparanase type, in a sample and in one preferred embodiment to a method for detecting compounds capable of modulating the activity of an endoglycosidase, and in particular of an endoglycosidase having activity of the heparanase type.

Endoglycosidases are enzymes capable of catalyzing cleavage reactions within glycosidic chains.

Heparanase is an enzyme capable of cleaving polymers comprising glycosaminoglycan (GAG) units, such as, for example, heparan sulfate glycosaminoglycans (HS-GAG or HS).

Heparan sulfate proteoglycans (HS-PG) are complex macromolecules associated with the cell surface or the extracellular matrix (ECM) of a wide variety of tissues and cells of human and nonhuman origin (David G. FASEB J. 7:1023-1030, 1993; Bernfield M. et al., Ann. Rev. Cell Biol. 8: 365-393, 1992; Bernfield M. et al., Ann. Rev. Biochem. 68: 729-777, 1999; David G. et al., Matrix Biol. 17:461-463, 1998; Kjellen L. et al. Annu. Rev. Biochem. 60: 443-475, 1991; Esko J. et al., Clin. Invest. 108:169-173, 2001; Kuschert G. S. et al., Biochemistry 38:12959-12968, 1999).

The principal structure of HS-PG consists of a core protein, to which one or several heparan sulfate chains are covalently attached. The linear polysaccharide chains generally consist of repeating disaccharide subunits composed of an L-iduronic acid (or alternatively glucuronic acid) and glucosamine. These disaccharides are substituted to a varying degree with N- and O-linked sulfate groups and N-linked acetyl residues. The substitution pattern, that results from the activity of various enzymes (e.g. C5-epimerase, 2-O-sulfotransferase, 6-O-sulfotransferase, 3-O-sulfotransferase, N-deacetylase/N-sulfotransferase etc.), leads, at least in part in a non-random fashion, to the formation of a domain structure within the HS chain that allows the specific interaction with a large number of ligands, like growth factors, chemokines etc. (Esko J. et al., Annu. Rev. Biochem. 71: 435-471, 2002; Handel T. M., Annu. Rev. Biochem. 74:385-410, 2005; Lindahl U. et. al., J. Biol. Chem. 259:12368-12376, 1984). HS chains can exhibit great diversity, due to the variable number of disaccharide units and to their sequence (resulting from the different substitutions that lead to a domain structure), which can differ from one chain to the other. Heparin has the same basic disaccharide structure than HS, but differs from HS in that it is more highly sulfated and contains more of the isomeric variant iduronic acid (David G. FASEB J. 7:1023-1030, 1993; Bernfield M. et al., Ann. Rev. Cell Biol. 8: 365-393, 1992; Bernfield M. et al., Ann. Rev. Biochem. 68: 729-777, 1999; David G. et al., Matrix Biol. 17:461-463, 1998; Kjellen L. et al., Annu. Rev. Biochem. 60: 443-475, 1991; Esko J. et al., Clin. Invest. 108:169-173, 2001; Kuschert G. S. et al., Biochemistry 38:12959-12968, 1999, Esko J. et al., Annu. Rev. Biochem. 71: 435-471, 2002; Handel T. M. et al., Annu. Rev. Biochem. 74:385-410, 2005).

The ECM of the various tissues is composed of a variety of matrix proteins, e.g. different types of collagens, etc., and different proteoglycans, resulting in a complex tissue architecture.

The basement membrane (basal lamina) is composed of a complex network of different types of laminin, nidogen and type IV collagen, that interact with the highly charged HS chains of different heparan sulfate proteoglycans embedded in this network (Paulsson M. Crit. Rev. Biochem. Mol. Biol. 27: 93-107, 1992; Timpl R.,et al. Matrix Biol. 14: 275-281, 1994; Timpl R. Curr. Opin. Cell. Biol. 8:618-624, 1996; Groffen A. J., Nephrol. Dial. Transplant. 14, 2119-2129, 1999; Yurchenko P. D., FASEB J. 4: 1577-1590, 1990; Colognato H. et al. J. Cell Biol. 145, 619-31, 1999).

HS-PG participate in many biological functions, including organogenesis and growth control, cell adhesion and migration, signaling, inflammation, wound healing, angiogenesis, tumor invasion and metastasis (David G. FASEB J. 7:1023-1030, 1993; Bernfield M. et al., Ann. Rev. Cell Biol. 8: 365-393, 1992; Bernfield M. et al., Ann. Rev. Biochem. 68: 729-777, 1999; David G. et al., Matrix Biol. 17:461-463, 1998; Kjellen L. et al., Annu. Rev. Biochem. 60: 443-475, 1991; Esko J. et al., Clin. Invest. 108:169-173, 2001; Kuschert G. S. et al., Biochemistry 38:12959-12968, 1999, Esko J. et al., Annu. Rev. Biochem. 71: 435-471, 2002; Handel T. M. et al., Annu. Rev. Biochem. 74:385-410, 2005, Lindahl U. et. al., J. Biol. Chem. 259:12368-12376, 1984).

GAG cleavage by endoglycosidases, for example enzymes having activity of the heparanase type, participates in local degradation and remodeling of the ECM in all the processes described above. One important mechanism of these processes is the release of HS-bound cytokines, chemokines, growth factors etc. by cleavage of GAG chains, especially of the HS type (Roberts R. et al., Nature 332, 376-378, 1988; Saksela O. et al., J. Cell Biol. 107, 743-751, 1988).

Heparanase, for example produced by platelets, inflammatory cells or tumor cells can contribute to local degradation of the basement membrane and thus facilitate cell migration and passage across the blood vessel wall (Roberts R. et al., Nature 332, 376-378, 1988; Saksela O. et al., J. Cell Biol. 107, 743-751, 1988). In this process other enzymes, like matrix metalloproteinases may be involved, too. Whereas normally this mechanism allows inflammatory cells, like neutrophils, to reach the site of inflammation within a tissue, the same mechanism is used by tumor cells to produce metastatic foci.

GAG cleavage by endoglycosidases is not restricted to passage of basement membrane, but for example is a major process of tissue invasion by tumor cells (Vlodaysky I. et al., J. Clin. Invest. 108:341-347, 2001; Parish C. R. et al., Biochim Biophys Acta 1471, 99-108, 2001; Vlodaysky I. et al., Cancer Biol. 12: 121-129, 2002).

Heparanase activity has been reported in several tissues and cell types, including liver, placenta, activated T lymphocytes, B lymphocytes, neutrophils and monocytes, platelets, fibroblasts and umbilical vein endothelial cells (Vlodaysky I. et al., J. Clin. Invest. 108:341-347, 2001; Parish C. R. et al., Biochim Biophys Acta 1471, 99-108, 2001; Vlodaysky I. et al., Cancer Biol. 12: 121-129, 2002; Oldberg A. et al., Biochemistry 19: 5755-5762, 1980; Freeman C. et al., Biochem. J. 330:1341-1350, 1998).

Heparanase has been isolated and purified from several sources, like human platelets, by different research groups (Vlodaysky I. et al., J. Clin. Invest. 108:341-347, 2001; Parish C. R. et al., Biochim Biophys Acta 1471, 99-108, 2001;

Vlodaysky I. et al., Cancer Biol. 12: 121-129, 2002; Oldberg A. et al., Biochemistry 19: 5755-5762, 1980; Freeman C. et al., Biochem. J. 330:1341-1350, 1998).

Heparanase has been cloned from several sources by different research groups (Vlodaysky I. et al. Nature Med. 5:793-802, 1999; Hulett M. D., Nature Med. 5: 803-809, 1999; Kussie P. H., Biochem. Biophys. Res. Commun. 261: 183-187, 1999; Toyoshima M. T., J. Biol. Chem. 274:24153-160, 1999). For example human heparanase was cloned from human placenta and a human hepatoma cell line (Vlodaysky I. et al. Nature Med. 5:793-802, 1999). The identification of a single functional heparanase is of major importance for the drug development. (Vlodaysky I. et al., J. Clin. Invest. 108: 341-347, 2001; Parish C. R. et al., Biochim Biophys Acta 1471, 99-108, 2001; Vlodaysky I. et al., Cancer Biol. 12: 121-129, 2002; Vlodaysky I. et al. Nature Med. 5: 793-802, 1999; Hulett M. D., Nature Med. 5: 803-809, 1999; Kussie P. H., Biochem. Biophys. Res. Commun. 261:183-187, 1999; Toyoshima M. T., J. Biol. Chem. 274: 24153-160, 1999; Zcharia E., FASEB J. 18: 211-221, 2005).

Characterization of the purified and cloned enzyme has shown that heparanase is synthesized as a 65 kDa inactive precursor that undergoes proteolytic cleavage, yielding 8 and 50 kDa protein subunits that heterodimerize to form an active enzyme (Bartlett M, et al. , Immunol. Cell Biol. 73: 113-124, 1995; Freeman C. et al., Biochem. J. 330:1341-1350, 1998)

Heparanase is preferentially expressed in human tumors and its over-expression in tumor cells confers an invasive phenotype in experimental animals. Heparanase up-regulation correlates with increased tumor vascularity and poor post-operative survival of cancer patients (Bartlett M, et al., Immunol. Cell Biol. 73: 113-124, 1995; Edovitsky E., J. Natl. Cancer Inst. 96:1219-1230, 2004; Takaoka M. et al., Lab. Invest. 83: 613-622, 2003; Nobuhisa T. et al., J. Cancer Res. Clin. Oncol. 131:229-237, 2005; Schoppmeyer K., Pancreatology 5, 570-575, 2005).

It has been shown that heparanase activity is linked to the metastatic potential of melanoma cell lines. For example, the metastatic potential of human and murine fibro-sarcoma and melanoma cell lines correlates with the heparanase activity of these cells (Vlodaysky I. et al., Cancer Res. 12:112-127,1989; Nakajima M. et al., Science 220: 611-613, 1983).

Inhibitors of heparanase, like heparin, as well as gene silencing of heparanase by siRNA can inhibit tumor metastasis and angiogenesis in experimental models (Edovitsky E., J. Natl. Cancer Inst. 96:1219-1230, 2004).

There is now a growing body of evidence that heparanase is a promising target for anti-cancer but also for anti-inflammatory drug development (Vlodaysky I. et al., J. Clin. Invest. 108:341-347, 2001; Parish C. R. et al., Biochim Biophys Acta 1471, 99-108, 2001; Vlodaysky I. et al., Cancer Biol. 12: 121-129, 2002; Vlodaysky I. et al. Nature Med. 5:793-802, 1999; Hulett M. D. et al., Nature Med. 5: 803-809, 1999; Kussie P. H. et al., Biochem. Biophys. Res. Commun. 261: 183-187, 1999; Toyoshima M. T. et al., J. Biol. Chem. 274: 24153-160, 1999; Zcharia E. et al., FASEB J. 18: 211-221, 2005; Edovitsky E. et al., J. Natl. Cancer Inst. 96:1219-1230, 2004; Takaoka M. et al., Lab. Invest. 83: 613-622, 2003; Nobuhisa T. et al., J. Cancer Res. Clin. Oncol. 131:229-237, 2005; Schoppmeyer K. et al., Pancreatology 5, 570-575, 2005)

According to the important role of heparanase for other biological functions like growth control, cell adhesion and migration, signaling, inflammation, wound healing and angiogenesis (Zcharia E., FASEB J. 18: 211-221, 2005), modulators of endoglycosidase activity and especially of heparanase enzyme activity will have potential also in other areas like chronic inflammation, autoimmunity, wound repair and angiogenesis.

Several groups have developed assays for the determination of heparanase activity, in particular with the aim of isolating novel compounds which might be used for example to inhibit metastasis in cancer patients.

In the past, most of the methods developed for assaying heparanase activity are based on radiolabeling of a substrate, like heparan sulfate, and analyzing the fragments generated after incubation with a sample containing the enzyme heparanase.

Radioactive isotopes like 35-S or 3-H can be incorporated into HS (GAG) by culturing cells in the presence of the appropiate radioactive precursors. Radiolabeled HS (GAG) are then used as a substrate.

Heparanase activity is determined for example by measuring either a decrease in the radioactivity or a reduction in the molecular weight of the labeled molecules. In the latter case, the substrate is analyzed by electrophoresis or by chromatography.

These methods have all the problems and limitations associated with the use of radioelements, in particular with respect to radioprotection. Furthermore, quantitative methods of this type are very laborous and time-consuming, for example when the decrease in size of the substrate is measured using gel permeation chromatography, collection of fractions and liquid scintillation counting. Therefore, these methods are not suitable for routine testing or high through-put screening. Application U.S. Pat. No. 6,207,402 (NZ 5044386) is an example of such methods.

Application U.S. Pat. No. 6,207,402 describes a method for assaying heparanase enzyme activity based on a separation step and the binding of native or partially degraded radiolabeled HS to the HS-binding protein chicken histidin-rich glycoprotein, that is immobilized to a sepharose-column.

Application WO 00/03306 describes methods to determine glycosidase activity, and in particular a method for screening anti-cancer or anti-inflammatory agents. The methods are based on studying the effect of a test agent on heparanase activity in the presence of a substrate of the HS type.

Heparanase activity is determined either by separating fragments of the cleaved substrate by column chromatography or by electrophoresis, using a colorimetric assay, in particular a colorimetric carbazole assay for detecting the reducing sugars formed during cleavage of the substrate or dimethylmethylene blue based assays.

A major disadvantage of these methods is their poor sensitivity, e.g. as much as 0.25-4 µg of partially purified recombinant heparanase and up to 50 µg heparan sulfate per well of the microtiter plate have to be used. Therefore, this assay is extremely expensive, too. Furthermore long incubation times of up to 17 hours were necessary with these methods. Thus, these methods are not suitable for routine testing or high throughput screening.

Application WO 00/77241 discloses a method for assaying heparanase activity based on the detection of HS (GAG) fragments derived by cleavage of labeled substrate by the enzyme heparanase present in the test sample.

The HS (GAG) substrate is attached first to a solid support (after oxidation of the substrate HS (GAG) by treatment with periodate), secondly the substrate is labeled for example with biotin. Thereafter, a cell regulator (for example a growth factor capable of binding to HS (GAG)) is bound to the biotin-labeled substrate HS (GAG).

After incubation with a test sample (containing heparanase and/or modulators of heparanase activity), cleaved fragments are immobilized by specific binding of biotin-labeled fragments from the substrate to a second solid support coated with avidin/streptavidin. The fragments thus separated can be detected, for example, using a labeled antibody specific for the binding group or for the growth factor, by colorimetric or fluorescence techniques. The signal measured is dependent on the heparanase activity in the sample.

Compared to the radioactive methods and to the colorimetric assay (WO 00/03306) described above, the assay described in WO 00/77241 is more sensitive and easier to handle. However, this assay still has major disadvantages.

First, the method is complex and requires several modification and binding steps to produce the substrate. Second, by some of these reactions and binding steps at least part of the heparanase cleavage sites of the substrate could be destroyed, masked (for example by the bound growth factor) or are inaccessible for the enzyme due to binding of the substrate to a solid phase. Therefore, only part of the heparanase activity will be measured using this assay. Third, the assay is complex and time consuming. Fourth, the assay is relative expensive due to the usage of growth factors, antibodies to growth factors etc. Therefore, this assay has major drawbacks for routine testing and especially for high throughput screening procedures.

Application US 2006/0127945 describes a method to determine endo-glycosidase enzyme activity, and in particular of the heparanase type, by measuring a signal resulting from a close proximity transfer (FRET) between two compounds attached to a substrate for the enzyme.

However, this assay has several disadvantages: First, HS exhibit very great heterogeneity both with regard to the sequence of the glycosidic units and the length of the chains, e.g. a chemically localized functionalization is difficult to achieve since the structure of HS varies from one molecule to another. Therefore, precise labeling of the substrate with donor and acceptor compounds is difficult. Second, due to these difficulties, reagents are relative expensive. Furthermore, this assay type requires expensive technical equipment. Third, although the sensitivity might be sufficient, the assay requires long incubation times (about 6 hours). Therefore, this assay has major drawbacks for routine testing and especially for high throughput screening procedures.

Application US 2003/0170746 discloses a method for testing potential inhibitors of heparanase activity, where a labeled substrate of the enzyme is bound to fibroblast growth factor (FGF), that was immobilized on a solid support. The substrate is labeled either by fluorescein (fluorescein isothyocyanate FITC or F2-FITC) or lanthanide chelates (europium). Interacting of a heparanase enzyme solution with the immobilized labeled substrate, in the presence or absence of the agent to be tested, leads to the release of a labeled fragment from the substrate that is detected in the solution remote from the solid support.

This assay, that has some features in common with that described in application US 2006/0127945, i.e. the use of fluorescence labels, has several advantages compared to that assay. For example, the complex and difficult double labeling of the substrate, that is required for the close proximity energy transfer, can be avoided. Furthermore, the assay is less time consuming.

However, this assay still has major drawbacks, for example (i) immobilization is achieved by a specific heparan sulfate binding protein, i.e. FGF. The binding domain for FGF is not evenly distributed within the heterogeneous substrate, i.e. heparan sulfate, but will vary from one molecule to the other. (ii) Cleavage sites for the enzyme heparanase on the labeled substrate will be blocked at least in part by binding to FGF.

(iii) Even more important is that the enzyme reaction is not carried out with a substrate in solution but rather with a solid phase bound substrate. Therefore, the accessability of heparanase cleavage sites on the substrate is impaired not only by bound FGF, but also by steric hindrance from the solid phase. The high enzyme/substrate ratios (on a weight base) that are necessary for this assay type that range from 7.5:1 (FITC-label) to 1:1 (europium-label) are strongly indicative for the existence of these problems.

Combinatorial chemistry has allowed to produce large libraries of compounds comprising more than hundred thousand substances. In order to test these molecules with respect to their endoglycosidase or heparanase modulating activity within a reasonable amount of time and at reasonable costs, it is necessary to use a simple, rapid, reliable test system that can be readily automated. As outlined above, techniques that have been developed previously to assay heparanase activity are not well suited for this purpose.

The present invention provides an assay for endoglycosidase or heparanase activity that fullfills all these criteria, e.g. the assay is extremely sensitive and reliable. Furthermore the assay is simple, rapid and requires minimal amounts of reagents and samples.

DETAILED DESCRIPTION OF THE INVENTION

The present invention relates to a method for determining endoglycosidase enzyme activity, and in particular of the heparanase type, in a sample (for example an extract of tissues or cells, whole blood, serum, plasma, CSF etc.), and in one preferred embodiment to a method for detecting compounds capable of modulating the activity of an endoglycosidase, in particular of an endoglycosidase having activity of the heparanase type.

The invention relates in particular to an assay for heparanase (format a), where the substrate is labeled with one member of a ligand-receptor pair. The corresponding member of the ligand-receptor pair will generate, either directly or indirectly, the signal to be measured. In one preferred embodiment of the method, compounds to be tested for their heparanase modulating activity were incubated in the first step together with heparanase and the labeled substrate.

In this assay the labeled substrate in solution is cleaved by heparanase in a dose-dependent manner. Depending on the size of the resulting fragment, the cleaved labeled substrate does no longer bind to a binding protein immobilized on a solid phase support, that in a preferred embodiment of the method is the polycationic protein protamine. The use of protamine as HS binding protein has several advantages compared to other HS binding proteins, like cytokines, growth factors etc. In this assay protamine can in particular be a protamine purified from sperm of different species, like salmon, herring, etc., a recombinant protamine, a low molecular weight protamine obtained for example after proteolytic cleavage of protamine, or a protamine-peptide. Furthermore, different protamine-like proteins, a class of arginine-rich proteins that belong to the histone family, can be used in this assay (Lewis, J. D. et al., Chromosoma 111: 473-482, 2003).

In the presence of a compound which inhibits (or activates) endoglycosidase activity, in particular activity of the heparanase type, the measured signal will be modified compared to the signal measured in the absence of this compound.

In order to develop an assay for endoglycosidase enzyme activity, and in particular enzyme activity of the heparanase type, the inventor had to overcome technical difficulties specifically encountered when assaying endoglycosidases, and in particular of the heparanase type.

The substrates of endoglycosidases, and in particular of the heparanase type, i.e. HS exhibit an extreme heterogeneity both with regard to the sequence of the disaccharide units (and their respective modifications) and the length of the chains. This is in particular due to the fact that HS are synthesized and modified by a large number of specific enzymes and are therefore difficult to produce by chemical synthesis. Since the structure of the HS can vary from one molecule to another, it is difficult to introduce localized functional groups.

The invention relates to a method for determining endoglycosidase enzyme activity comprising the following steps:

i. bringing a labeled substrate of an endoglycosidase in solution into contact with said endoglycosidase under conditions sufficient for degradation of the substrate by the endoglycosidase ii. separating degradation products from undegraded or partially degraded substrate by binding the undegraded or partially degraded substrate to a solid phase bound HS binding protein, preferably to the polycationic protein protamin iii. measuring the change in the amount of intact labeled substrate, a decrease in the amount of this substrate being representative of endoglycosidase activity in the sample.

After degradation of the labeled substrate by the endoglycosidase, and in particular by an enzyme of the heparanase type, degraded substrate will no longer bind to the binding protein, that in a preferred embodiment of the method is the solid-phase bound polycationic protein protamin. After removal of unbound substrate by washing, bound labeled substrate can be measured. In this method, the substrate is labeled directly or indirectly.

The term "direct labeling" is intended to mean attachment of a label, for example a fluorescent label, to a functional group present on, or previously introduced onto, or generated on the substrate or on at least one of the members of the ligand/receptor pair. A spacer can be introduced between the label and the substrate or at least one of the members of the ligand/receptor pair.

The term "indirect labeling" is intended to mean attachment of the label, to the substrate via the second member of a ligand/receptor pair. The label is selected either from the group of enzymes, that are in use for enzyme immuno assays, like peroxidase, alkaline phosphatase etc, or from the group of fluorescent, chemiluminescent, electrochemiluminescent or colorimetric labels.

In one preferred embodiment of this method, the substrate is labeled indirectly with biotin via the peptide stub of the peptido-HS and avidin coupled to peroxidase is used as the second member of the ligand receptor pair.

This method can be used to measure endoglycosidases capable of cleaving heparan sulfates, such as, for example, heparanase.

The method for determining endoglycosidase enzyme activity described above may make it possible to study the effects of modulation of this enzyme activity, exerted by compounds for which the testing of the influence on the enzyme activity is desired.

The expression "modulation of enzyme activity" is intended to mean inhibition or activation of this enzyme activity, regardless of the mechanism.

In one preferred embodiment the invention therefore relates to a method for detecting a compound capable of modulating enzyme activity of the endoglycosidase type, comprising the following steps:

i. bringing a substrate of an endoglycosidase in solution into contact with an endoglycosidase, in the presence or absence of the test compound, ii. measuring the change in the amount of intact substrate by time, and iii. comparing the change in the amount of substrate by time measured in the absence of the test compound with that measured in the presence of the test compound.

In this method, the endoglycosidase substrate and/or at least one of the other components can be directly or indirectly labeled as described above.

In the latter method, the endoglycosidase used can in particular be a heparanase chosen from recombinant heparanase, purified heparanase and nonpurified heparanase (for example a platelet extract). The enzyme is usually provided in at least a partially purified form.

The substrate used in the preceeding methods can be selected from heparan sulfate proteoglycans (HS-PG), heparin and peptido-heparan-sulfates (peptido-HS) or their derivatives. Peptido-HS are derived from HS-PG after proteolytic degradation of the core protein, for example by papain, resulting in a HS GAG chain with a short residual peptide-stub.

Substrate derivatives can be HS, heparin or HS-PG which have undergone minor modifications such as for example, but not limited to, selective desulfatation, graded N-acetylation, or reductive oxyamination, that do not interfere with the enzyme-substrate recognition, i.e. they can be cleaved by an enzyme having activity of the heparanase type (Naggi A. et al, J. Biol. Chem. 280: 12103-12113, 2005, Fernandez C. et al., Carbohydrate Res. 341: 1253-1265, 2006; Sandbäck-Pikas D, et al., J. Biol. Chem 273: 18770-18777, 1998, Ramsay S., et al. Carbohydrate Res. 333: 59-71, 2001).

The method according to the invention can be implemented using various formats. The following formats are the preferred formats.

Format [a]: the substrate is covalently attached to a first member of a ligand/receptor pair. The other member of the ligand receptor pair is coupled to an enzyme detection system, like the peroxidase system.

Format [b]: the substrate is covalently attached to a first member of a ligand/receptor pair. The other member of the ligand/receptor pair is labeled for example with a fluorescent label.

Format [c]: the substrate is covalently attached to a fluorescent, chemoluminescent or electrochemiluminescent label. In this format the signal from the labeled substrate bound to the solid phase is measured directly.

The "ligand-receptor pair" denotes two binding partners such as the pairs: biotin/avidin; biotin/streptavidin; hapten/antibody systems like DNP (dinitrophenol)/anti-DNP antibody or HA (influenza hemagglutinin peptide of 9 amino acids)/anti-HA antibody; GST (glutathione S-transferase)/anti-GST antibody; 6HIS (peptide consisting of 6 histidines)/anti-6HIS antibody; c-myc (peptide of amino acids 410-419 of the human c-myc protein)/anti-c-myc antibody, or FLAG (R) (peptide of 4 amino acids)/anti-FLAG (R) antibody. Other ligand-receptor pairs known by the skilled artisan can be used.

These "ligand/receptor" systems are well known to those skilled in the art and are mostly commercially available.

The member of the ligand-receptor pairs can be covalently attached to the substrate using a variety of reactional groups such as hydroxysuccinimide ester or hydroxy-sulfo-succinimide esters.

The method for detecting a compound capable of modulating enzyme activity of the heparanase type makes it possible to screen large libraries of products which can in particular be anti-heparanase antibodies, natural products, synthetic products, products from a library of compounds obtained by combinatorial chemistry, for example of peptides and proteins for their ability to modulate the enzyme activity.

Furthermore, the invention also relates to kits, containing the reagents usable or required to carry out the embodiments of the method according to the invention, and in particular the following elements:

A substrate which can be cleaved by an enzyme having activity of the heparanase type, in particular HS-(GAG) or peptido-HS (GAG) preferably labeled with a first member of a receptor/ligand pair Heparanase (i.e. recombinant heparanase, purified heparanase or nonpurified heparanase)

A detection system comprising the second member of the receptor ligand pair

A kit according to the invention (to measure heparanase activity) preferably contains:

The substrate heparan sulfate (peptido-HS) labeled with biotin (via the peptid stub)

Avidin (or streptavidin) coupled to peroxidase and a suitable substrate like orthophenylendiamine (OPD)

A protamine-coated solid phase, for example a microplate

In another embodiment a kit according to the invention (to test potential modulators of heparanase activity) preferably contains:

The substrate heparan sulfate (peptido-HS) labeled with biotin (via the peptid stub)

Avidin (or streptavidin) coupled to peroxidase and a suitable substrate like OPD Heparanase (chosen from recombinant heparanase, purified heparanase, non-purified heparanase)

A protamine-coated solid phase, for example a microplate

The method according to the invention has many advantages compared to the methods of the prior art, and in particular:

The method is a non-radioactive assay.

The assay is very simple to carry out since it comprises only few steps and will be completed in less than 3 h.

The method does not require expensive technical equipment.

The enzymatic reaction of the endoglycosidase, and in particular of the heparanase, ranase, with the labeled substrate is performed in solution and not with a substrate coupled to a solid phase. Therefore, problems with steric hindrance and a lack of accessability of cleavage sites on the substrate for the enzyme are avoided.

No chemical treatment or modification of the GAG-chain is required. In this assay format only the peptid stub (of the original core protein) is labeled by a small ligand, for example biotin. Therefore, heparanase cleavage sites of the HS (GAG) are readily accessible, as outlined above.

The method according to the invention preferably uses as HS binding protein the poly-cationic protein protamine instead of other ligands for HS (or heparin), for example of growth factors, like bFGF. In contrast to the binding domains for these specific ligands, that in general have a restricted expression pattern on HS chains, the anionic groups, e.g. sulfate groups, that mediate the ionic interaction of HS and protamine, are evenly distributed on the polyanionic HS chains. Therefore, the assay is more sensitive and less vulnerable to changes of the composition of the substrate with respect to the specific binding domains.

In addition, the use of growth factors, cytokines etc. as specific binding proteins for the labeled substrate will lead to high costs of the assay.

In contrast to an immuno assay, that uses for example monoclonal antibodies to different epitopes of the heparanase molecule, in the assay according to the invention the functional activity of heparanase in a sample is measured instead of the heparanase concentration. In contrast, an immunoassay will detect, dependent on the assay design and the respective antibodies, also inactive or degraded heparanase. Therefore, an immunoassay does not allow to analyse modulators of endoglycosidase activity.

The volumes used are very small (50 µl per well, in example 4 and 5). However, the assay can be miniaturized further (for example using 384 well plates) and this makes it possible to save on reagents, for example:

As little as 10 ng of substrate is used in example 4. However, the assay has been performed successfully also with 2 ng of labeled substrate (data not shown). In contrast, in application US 2006/0127945 at least 30 ng of substrate, in application US 2003/0170746 between 18.75 ng (europium-labeled substrate) and 150 ng of fluorescein-labeled substrate, and in application WO 00/03036 from 5 to 50 µg of substrate are used.

The same is true for the amount of enzyme used in the assay. In example 4 less than 0.1 µU (equivalent to 0.15 ng) of the enzyme heparanase are used, whereas in application WO 00/03036 3 µg heparanase (corresponding to 2.1 mU) were used (with incubation times of up to 24 h) and in application US 2003/0170746 at least 20 ng of recombinant heparanase were used. In contrast, in application US 2006/0127945 the endoglycosidase activity was tested with the bacterial enzyme heparitinase III (heparinase III from *Flavobacterium heparinum*) instead of heparanase and therefore cannot be compared directly.

The incubation times for all steps are very short, as is shown in example 4, i.e. the enzyme reaction requires 1 h of incubation (but can be reduced further). In contrast, in application WO 00/03036 the enzyme reaction requires at least 4 h and in application US 2006/0127945 at least 5 h in order to obtain a signal.

The method according to the invention therefore makes it possible to dertermine heparanase activity in a sample or to rapidly screen libraries of molecules capable of modulating heparanase activity.

Thus, for embodiments of the method according to the invention, there are important applications in the field of in vitro diagnosis but also in that of high throughput-screening in the pharmaceutical industry.

BRIEF DESCRIPTION OF THE FIGURES

FIG. 1: The bar graph shows the dose-dependent binding of biotin-labeled HS to the protamin-coated solid phase.

FIG. 2: The bar graph shows the dose-dependent degradation of biotin-labeled heparan sulfate by human heparanase, isolated from polymorphonuclear neutrophils (PMN).

FIG. 3: The bar graph shows the dose-dependant inhibition of heparanase activity by heparin

EXAMPLES

The following examples illustrate in a nonlimiting manner the preferred embodiments of the methods according to the invention:
Experimental Section
The following abbreviations are used:
HS: heparan sulfate
NHS: N-hydroxysuccinimide
PBS: phosphate buffered saline POD: horseradish-peroxidase
OPD: orthophenylendiamine For the examples, the substrate is functionalized using the $NH_2$ functions of the peptido-HS (peptido-HS is produced by digestion of core proteins of purified heparan sulfate proteoglycans with a proteolytic enzyme like papain, resulting in glycosaminoglycan chain with short peptide stubs)

Example 1

Preparation of a-HS-Biotin Substrate
  Reagents Used:
    Solution of HS (Sigma H9902) at 5 mg/ml: 5 mg HS +1 ml PBS (Gibco).
    Solution of Sulfo-NHS-LC-Biotin (EZ-Link® Sulfo-NHS-LC-Biotin) at 20 mM: 11 mg Sulfo-NHS-LC-Biotin (Pierce) +1 ml PBS (Gibco)
  Biotin Labeling
1 ml of a solution of HS at 5 mg/ml (Sigma) are mixed with 0.1 ml of 20 mM Sulfo-NHS-LC-Biotin. The mixture is incubated for 18 h at 37° C. Excess biotin is removed using a 5 ml Zeba™ Desalt Spin Column (Pierce), equilibrated with PBS. By this, 1 ml of solution containing the biotinylated HS, hereinafter referred to as biotin-HS, was obtained.

Example 2

Determination of the Final Molar Ratios
  Assaying the Biotin:
  The biotin concentration is measured using a photometric assay based on the competition of biotin-HS and HABA (4'-hydroxyazobenzene-2-carboxylic acid) for binding to avidin. Absorbance of the HABA/avidin complex is measured at 500 nm. Subsequently, biotin-HS is added and the decrease of absorbance is recorded. Known amounts of biotin-labeled POD are used as standard to calculate the molar ratio of biotin and HS.

Example 3

Testing the Binding of Biotin-labeled HS to a Protamine-coated Solid Phase
  Reagents Used:
  Biotin-labeled HS (see above, example 1)
  Protamine sulfate, from herring, grade III, Sigma P4505
  Avidin-POD (Sigma A 3151)
  PBS/0.01% Tween-20
  OPD (Dako S 204530)

A solid phase, for example a microtiterplate, is coated with protamine by incubation of 100 µl/well of a 0.003% solution of protamine sulfate at 37° C. for 24 hours. Thereafter, plates were washed 3 times with A dest. and stored in the dark.

The binding capacity of the solid phase, e.g. the wells of the microplate, was analyzed by incubation of increasing amounts of biotin-labeled HS (0.1-100 ng/ml) for 60 min at room temperature Plates were washed 3 times with buffer (PBS/0.01% Tween 20) and Avidin-POD (1 µg/ml in PBS/5% BSA) was added.

After 15 min plates were washed 5 times with citrate/phosphate-buffer (pH 6.2; 34.7 mM citric acid/66.7 mM $Na_2HPO_4$) and 100 µl OPD-solution (0,667 mg/ml) was added.

After 15 min the reaction was stopped by addition of 100 µl of 0.5 Mol $H_2SO_4$. OD was measured at 490 nm using a microplate reader.

FIG. 1 shows the dose-dependent binding of biotin-labeled HS to the protamine-coated solid phase.

Example 4

Assaying Activity of the Heparanase Type
  Reagents Used:
  same as in example 3
  Heparanase from polymorphonuclear neutrophils, isolated from peripheral blood using standard ficoll density gradient procedures, prepared according to the method described by the group of Vlodaysky (Matzner Y. et al., J. Clin. Invest. 76:1306-1313, 1985). 10 µl of this heparanase solution in 20 mM citrate/phosphate buffer (pH 6.2) are equivalent to 0.1 µU or 0.15 ng of recombinant enzyme heparanase.

The enzyme reaction is carried out by mixing 50 µl of biotin-labeled HS at 0.2 µg/ml with increasing amounts of heparanase (0.5-20 µl heparanase, representing 0.01 to 0.2 µU). Samples were brought to a volume of 100 ml by addition of 20 mM citrate/phosphate buffer (pH 6.2).

This mixture is left at room temperature for 1 h.

Samples (50 µl of the samples) were transferred to the protamin-coated microplate and incubated for 1 hour at room temperature. The following steps are identical to those described for example 3.

The results are expressed in FIG. 2, which shows the change in the signal for an increase in concentration of the enzyme heparanase.

The decrease in the signal correlates perfectly with the increase in the enzyme activity, i.e. the cleavage of the biotin-labeled HS substrate.

Example 5

Determination of a Modulator, for example an Inhibitor, of Enzyme Activity of the Heparanase Type
  Reagents used:
  same as in example 4
  heparin (sodium salt, unfractionated heparin from porcine intestinal mucosa (grade Ia, 170 USP/mg) (Sigma H 3393)

The same procedure as in example 4 is carried out, but increasing amounts of the modulator, i.e. the inhibitor were added to the reaction mixtures of heparanase (constant) and biotin-labeled HS (constant).

In this experiment the amount of 10 µl heparanase was selected from the dose-dependancy curve (FIG. 2) to assure that after 1 hour about 80-90% of biotin-labeled HS is degraded by the heparanase. This allows to detect the activity of inhibitors like heparin in the linear part of the curve.

In this experiment heparin was used as inhibitor at concentrations of 0.1-5 ng/ml.

The percentage inhibition (or activation) of the enzyme due to the test compound (i.e. the inhibitor) is determined, by comparison of the results obtained in the presence and in the absence of the test compound.

Inhibition was calculated according to the following formula $$\% \text{ Inhibition} = \frac{OD_{(x^*)}}{OD(\text{max}^*)} \times 100$$

where $OD_{(max)}$ is the $OD_{(490\ nm)}$ for biotin-labeled HS (10 ng/ml) in the absence of heparanase and inhibitors. $OD_{(max^*)}$ is set to $OD_{(max)}-OD_{(hep-10)}$, where $OD_{(hep-10)}$ is the $OD_{(490\ nm)}$ that results after degradation of biotin-labeled HS by 10 µl heparanase. $OD_{(x)}$ is then the $OD_{(490\ nm)}$ measured for the concentration x of an inhibitor. $OD(x^*)$ is set to $OD_{(x)}-OD_{(hep-10)}$. Results are given as percent inhibition.

The results are expressed in FIG. 3, which shows the change in the signal for an increase in concentration of the inhibitor, i.e. heparin.

Format [a] used in the examples 1-5 is therefore entirely suitable for a method to measure endoglycosidase enzyme activity, and in particular of the heparanase type, but also for testing a modulator of this enzyme activity.

The invention claimed is:

1. A method for determining endoglycosidase enzyme activity comprising the following steps:
    i. bringing an endoglycosidase substrate into contact with an endoglycosidase containing sample under conditions sufficient for degradation of the substrate by endoglycosidase,
    ii. separating degradation products from intact or partially degraded substrate by binding the intact or partially degraded substrate to a solid phase bound heparan sulfate binding protein, and
    iii. measuring a decrease in an amount of intact substrate, said decrease relating to the endoglycosidase activity in the sample,
wherein the substrate is directly or indirectly labeled with a first member of a ligand/receptor pair, and the amount of intact substrate is determined by measuring a signal emitted by a detection system bound to a second member of the ligand receptor pair.

2. The method as claimed in claim 1, wherein the first member of the ligand/receptor pair is biotin and the second member of the ligand receptor pair is avidin or streptavidin coupled to an enzyme as part of the detection system, or wherein the ligand/receptor pair is selected from the group of hapten/antibody pairs consisting of: DNP/anti-DNP antibody; GST/anti-GST antibody; 6HIS/anti-6HIS antibody; c-myc/anti-c-myc antibody; FLAG(R)/anti-FLAG(R) antibody; and HA/anti-HA antibody.

3. The method as claimed in claim 1 wherein said sample is selected from the group consisting of an extract of tissues or cells, whole blood, serum, plasma and cerebrospinal fluid.

4. A method according to claim 1 further comprising the following step:
    iv. comparing an amount of intact substrate measured in the absence of a test compound with an amount of intact substrate measured in the presence of the test compound, wherein a difference in the amount of intact substrate indicates that the test compound is capable of modulating an endoglycosidase enzyme activity.

5. The method as claimed in claim 1, wherein the endoglycosidase is an enzyme of the heparanase type selected from the group consisting of recombinant heparanase, purified heparanase and nonpurified heparanase.

6. The method as claimed in claim 1, wherein the substrate is selected from the group consisting of heparan sulfate proteoglycans, extracellular matrix-associated heparan sulfates, heparin, heparan sulfates and their respective derivatives.

7. The method as claimed in claim 1, wherein the heparan sulfate binding protein is selected from the group consisting of protamine and arginine-rich, protamine-like proteins from the histone family, wherein the heparan sulfate binding protein is selected from the group consisting of natural proteins, proteins purified from sperm of different species, low molecular weight forms of these proteins, low molecular weight forms of these proteins derived by proteolytic cleavage, peptides and recombinant proteins.

8. The method as claimed in claim 6, wherein the substrate is covalently attached to a first member of a ligand/receptor pair and the second member is coupled to an enzyme as part of a detection system.

9. The method as claimed in claim 8, wherein the second member of the ligand/receptor pair is labelled with a fluorescent, chemiluminescent or electrochemiluminescent label.

10. The method as claimed in claim 6, wherein the substrate is covalently attached to a fluorescent, chemiluminescent or electrochemiluminescent compound and the fluorescence or luminescence signal of the substrate bound to the heparan sulfate binding protein is measured directly.

11. The method as claimed in claim 4, wherein said compound is selected from the group consisting of anti-heparanase antibodies, natural products, synthetic products, products from a library of compounds obtained by combinatorial chemistry, peptides and proteins.

12. A kit for carrying out the method as claimed in claim 1, comprising the following components:
    (a) a substrate which can be cleaved by an enzyme having activity of the heparanase type,
    (b) heparanase,
    (c) a detection system comprising a second member of the receptor/ligand pair, coupled to an enzyme, and
    (d) a heparan sulfate binding protein.

13. A kit as claimed in claim 12 comprising:
heparan sulfate,
avidin or streptavidin coupled to peroxidase and a peroxidase substrate, and
a protamine-coated solid phase.

14. A kit as claimed in claim 13 further comprising:
heparanase selected from the group consisting of recombinant heparanase, purified heparanase and non-purified heparanase.

15. The method of claim 1, wherein said solid phase bound heparan sulfate binding protein is protamine.

16. The method of claim 5, wherein the endoglycosidase enzyme is provided in at least a partially purified form.

17. The kit of claim 12, wherein said enzyme having activity of the heparanase type is HS-(GAG) or peptide-HS-(GAG).

18. The kit of claim 17, wherein said HS-(GAG) or peptide-HS-(GAG) is labeled with a first member of a receptor/ligand pair.

19. The kit of claim 12, wherein said heparanase is selected from the group consisting of recombinant heparanase, purified heparanase and non-purified heparanase.

20. The method of claim 12, wherein said second member of the receptor/ligand pair is avidin peroxidase or streptavidin peroxidase.

21. The method of claim 12, wherein said heparan sulfate binding protein is bound to a solid phase.

22. The method of claim 13, wherein said heparan sulfate is peptido-HS, labeled with biotin.

23. The method of claim 13, wherein said protamine-coated solid phase is a microplate.

* * * * *